United States Patent [19]

Jeretin et al.

[11] 4,434,160

[45] Feb. 28, 1984

[54] NUTRIENT SOLUTION FOR COMPLETE PARENTERAL FEEDING AND FOR INCREASED ENERGY PRODUCTION

[75] Inventors: Stojan Jeretin, Ljubljana, Yugoslavia; Karl Groke, Eggersdorf; Horst E. Musil, Graz, both of Austria

[73] Assignee: Leopold & Co. Chem. Pharm. Fabrik Gesellschaft m.b.H., Graz, Austria

[21] Appl. No.: 281,050

[22] Filed: Jul. 7, 1981

[30] Foreign Application Priority Data

Jul. 11, 1980 [DE] Fed. Rep. of Germany ....... 3026368

[51] Int. Cl.$^3$ .................. A61K 31/70; A61K 31/185; A61K 31/205
[52] U.S. Cl. ................................... 424/180; 424/316; 424/319
[58] Field of Search ........................ 424/316, 319, 180

[56] References Cited

U.S. PATENT DOCUMENTS 3,810,994  5/1974  Wiegand .
4,320,145  3/1982  Cavazza .............................. 424/316

FOREIGN PATENT DOCUMENTS 639532  5/1964  Belgium .
1435916  5/1976  United Kingdom .
2021410  12/1979  United Kingdom .

*Primary Examiner*—Stanley J. Friedman
*Attorney, Agent, or Firm*—Wenderoth, Lind & Ponack

[57] ABSTRACT

A nutrient solution for complete parenteral feeding and for increased energy production, for administration to patients in the post-aggression phase, which contains, in aqueous solution, per 25 parts by weight of an aminoacid mixture, at most 50 parts by weight of glucose or glucose substitutes or both, and 0.8–1.2 parts by weight of L-carnitine in the form of one of its salts. Preferably, the solution also contains electrolytes.

7 Claims, No Drawings

NUTRIENT SOLUTION FOR COMPLETE PARENTERAL FEEDING AND FOR INCREASED ENERGY PRODUCTION

The present invention relates to a nutrient solution, containing aminoacids, for the complete parenteral feeding and treatment of patients in the post-aggression phase, which solution ensures adequate aminoacid supply to the body and increased energy production.

The parenteral feeding of patients who for one reason or another cannot take any food is constantly increasing in importance. In such feeding, it is desired not only to meet the carbohydrate requirement of the body but also to maintain the functional proteins and structural proteins through supplying aminoacids.

Especially in the case of patients in the post-aggression phase, ie. after accidents, or in a post-operative condition, there is, to compensate the increased proteolysis, a high aminoacid requirement, for example of 1.5–2 g of aminoacids per kg of body weight per day. If, however, aminoacids are simply administered in this amount, it does not ensure their incorporation into the body's own protein, since such incorporation requires energy, namely 120–200 kcal for the incorporation of 1 g of nitrogen, and particularly in the case of severely catabolic patients such energy is not available.

To take account of this situation, it is therefore already known that energy sources must be administered additionally to the aminoacids, see, for example, H. Förster, Internist 19, 2–19 (1978). Such energy sources are carbohydrates, fats and alcohol, and in most cases combinations are employed, since each of the three energy sources has disadvantages, especially if used in too high a dosage.

Thus, for example, glucose is effective as a general energy source only if more is administered than the glucose demand of the exclusively glucose-dependent body tissues. The latter demand is usually 120–150 g and at most 200 g per day. Accordingly, more than 200 g of glucose per day must be administered as an energy source. Such high doses can, however, especially in the case of patients in the post-aggression phase, lead to hyperglycemia and to excretion of glucose in the urine, and also to an increase in the lactate concentration in the blood. Higher amounts of fructose are better tolerated, but even their administration can result in an increase in the lactate concentration. Sorbitol behaves similarly to fructose and furthermore has an osmotic effect at high concentration. All sugar substitutes (fructose, sorbitol and xylitol) exhibit increased rates of phosphorylation with decrease in the serum phosphate concentration and possible increase in the serum uric acid concentration.

Accordingly, the principal energy source must be sought amongst the fats, but these can also not be administered without complications. Thus, for example, fat administration leads to disturbances in fat utilization, which in turn result in a great increase in the fat concentration in the serum, which can entail liver damage and blockade of the reticulo-endothelial system.

To use ethyl alcohol as an energy source presents all sorts of problems and is contra-indicated in cases of liver damage, though, without doubt, it has a high energy content. The main disadvantage is its high osmotic pressure which in turn can lead to thrombo-phlebitis. Accordingly, there did not exist a satisfactory solution to the problem of energy supply in parenteral feeding, and instead serious disadvantages often had to be accepted.

It is known, on the other hand, that the natural substance carnitine, namely $\beta$-hydroxy-trimethylammoniumbutyrobetaine possesses, in addition to other pharmacologically utilizable effects, an effect on the fat metabolism in the sense that it lowers the lipid concentration in the blood. This effect is based on the fact that carnitine favors the transport of fatty acids into the mitochondria. Accordingly, carnitine has already been employed in the control of adiposity, whilst on the other hand it has served to prevent degeneration phenomena, such as arteriosclerosis, which result from an increased concentration of lipids in the blood (U.S. Patent Specification No. 3,810,994). For this purpose, it has also been employed together with fat-cleaving agents (British Patent Specification No. 1,435,916). On the other hand, it has also already been used to improve the utilization of parenterally administered fat emulsions, see Belgian Patent Specification No. 639,532 and British Patent Specification No. 2,021,410.

It has now been found, surprisingly, that it is possible to provide complete nutrient solutions, for complete parenteral feeding, especially in the post-aggression phase, which permit optimum utilization of the aminoacids administered, because the requisite amount of energy is available at the same time, without having to accept the disadvantages described above. Accordingly, these solutions do not contain any fat emulsions and contain glucose or glucose-substitutes only to the extent that they are necessary for the carbohydrate supply of the body. The fact that the solutions according to the invention nevertheless provide the energy required for building the aminoacids into the body is due to the fact that a certain amount of L-carnitine is present per part by weight of aminoacids and is able, especially in the post-aggression phase, to mobilize the body's own depot fat and, through catabolism thereof, to provide the requisite energy.

Accordingly, the present invention relates to an aqueous composition for the complete parenteral feeding and treatment of patients in the post-aggression phase, comprising per 25 parts by weight of a mixture of amino-acids which contains at least all the essential amino-acids and can additionally also contain non-essential aminoacids, at most 50 parts by weight of glucose or glucose substitutes from the group of fructose and sugar alcohols, or a mixture of glucose and glucose substitutes and 0.8–1.2 parts by weight of L-carnitine as an inner salt or as a pharmaceutically tolerated addition salt with an acid, and containing no fat.

In choosing the composition of the aminoacid mixture in the nutrient solution according to the invention it is advisable to ensure that the essential aminoacids are present substantially in those ratios which correspond to the body's demand. There are different opinions concerning this demand, and it is fully within the scope of the present invention to base the nutrient solution according to the invention on whichever one of the known aminoacid patterns (for example that given by Rose or that given by Knauff) appears most suitable. For the post-aggression phase, where special metabolic conditions exist, an aminoacid mixture corresponding to the following limits has proved particularly suitable:

0.8–1.05 parts by weight of L-isoleucine
1.4–1.5 parts by weight of L-leucine
1.4–1.65 parts by weight of L-lysine
0.5–1.2 parts by weight of L-methionine 1.25–1.4 parts by weight of L-phenylalanine
0.7–1.05 parts by weight of L-threonine
0.35–0.375 parts by weight of L-tryptophane
1.0–1.5 parts by weight of L-valine
2.0–2.8 parts by weight of L-arginine
1.0–1.5 parts by weight of L-histidine
3.5–4.0 parts by weight of L-analine
0.35–0.55 parts by weight of L-aspartic acid
0.1 part by weight of L-cysteine
2.0–2.25 parts by weight of L-glutamic acid
1.5–2.3 parts by weight of glycine
0–0.625 part by weight of L-ornithine
2.2–2.8 parts by weight of L-proline
1.1–1.4 parts by weight of L-serine
0–1.5 parts by weight of L-tyrosine.

The ranges stated are to be understood in the sense that the amounts of the individual aminoacids are chosen within the limits shown, but bearing in mind that in total 25 g of aminoacid mixture must result.

The nutrient solution according to the invention can be formulated at any concentration which the solubility conditions permit, that is to say the solution can be of 3% or 4%, but equally well 10%, strength, calculated in terms of aminoacid content. Accordingly, a 10% strength solution thus contains 100 g of aminoacids, and 3.2–4.8 g of carnitine, per liter. The only important point at all concentration levels is that the proportion according to the invention of 0.8–1.2 parts by weight of carnitine per 25 parts by weight of aminoacid mixture is met. The solubility conditions can inter alia also be improved if, for example, the sparingly soluble aminoacids tyrosine and cysteine are present in the form of readily soluble derivatives, for example acyl derivatives and especially acetyl derivatives, in the solution according to the invention.

Examples of pharmaceutically tolerated salts of carnitine which can be administered are the hydrochloride, the acetate and the malate.

The limit, according to the invention, of glucose and/or glucose substitutes, namely maximally 50 parts by weight per 25 parts by weight of aminoacid mixture, is calculated so that the amount in 1 liter of a solution containing 10% of aminoacids just corresponds to the amount considered to be the maximum value of the body's own demand per day under exceptional conditions and accordingly reliably exceeds the normal body demand. This proportion has been chosen since, especially in the post-aggression phase, it is essential that the glucose-dependent organs should be adequately supplied with this compound. Of course, the amount of glucose or the amount of glucose substitutes can also be kept lower and can advantageously be adapted to the various indications. Equally, any desired variation in respect of the choice of glucose, fructose or sugar alcohols, such as sorbitol or xylitol, or of mixtures of these substances, is possible.

Particularly in the post-aggression phase it can be advantageous, especially in order to maintain the homeostasis, to supply electrolytes simultaneously with the nutrient solution. They on the one hand serve, for example, to maintain the acid-base equilibrium, whilst on the other hand potassium is absolutely essential for protein synthesis. In addition, there are of course also a number of other, known advantages.

Advantageously, the solution according to the invention contains 2.5 parts by weight of electrolytes per 25 parts by weight of aminoacids. Preferably, it contains $Na^+$, $Ca^{++}$, $Mg^{++}$, $Zn^{++}$ and $K^+$, as well as chloride ion and acetate ion.

The nutrient solution according to the invention is not only intended as a nutrient solution, but is also of such composition that it permits an improvement in the general condition of the patient, especially in the post-aggression phase, that is to say after accidents, burns, operations, etc., so that accordingly treatment of this condition is also provided. This improvement is achieved by the fact that as a result of the carnitine content according to the invention, free fatty acids are introduced into the mitochondria and accordingly the conversion of triglycerides is increased. This achieves increased energy production and furthermore the supply of aminoacids, which, because of the simultaneous adequate generation of energy, can also be correctly utilized by the body, provides adequate substrates for the energy-supplying citrate cycle. Since the general supply of energy results from the mobilization of the depot fat, the glucose supplied is totally available for the demand of the glucose-dependent tissue. All this leads to more rapid recovery of the patient. In parenteral feeding, substitution of phosphate is fundamentally necessary. This can advantageously be achieved by adding the requisite amount of phosphate to the particular infusion, with due attention to the maximum dosage limits for phosphate.

The solution according to the invention is therefore indicated as an infusion solution for parenteral feeding and treatment of patients in the post-aggression phase in all cases where the patient still has mobilizable depot fat in the body. If this depot fat is lacking, the solution according to the invention can of course not develop its effect. However, particularly in treatment following accidents, burns and other traumatic conditions, the presence of such depot fat can be assumed, so that treatment with the solution according to the invention is particularly indicated especially in cases of this type, whilst such cases are particularly critical for conventional parenteral feeding because of metabolism misdirection (lipolysis, glucose utilization disturbance and the like).

The examples which follow serve to explain the present invention in more detail, without implying any limitation thereof.

EXAMPLE 1

A nutrient solution having an aminoacid concentration of 10% is prepared from the following aminoacids:
L-Isoleucine: 4.200 g
L-Leucine: 5.600 g
L-Lysine: 5.600 g
L-Methionine: 4.800 g
L-Phenylalanine: 5.600 g
L-Threonine: 2.800 g
L-Tryptophane: 1.400 g
L-Valine: 4.200 g
L-Arginine: 11.200 g
L-Histidine: 4.200 g
L-Alanine: 14.000 g
L-Aspartic acid: 1.400 g
L-Cysteine: 0.390 g
L-Glutamic acid: 8.000 g
Glycine: 9.200 g
L-Proline: 11.200 g
L-Serine: 5.600 g These aminoacids, together with 4.000 g of L-carnitine, are dissolved, with stirring, in 750 ml of warm infusion water, the L-cysteine being employed as N-acetyl-L-cysteine in an amount corresponding to the abovementioned amount of cysteine, and L-lysine being employed in the form of the corresponding amount of L-lysine-L-glutamate.H$_2$O. 75.000 g of glucose and 75.000 g of fructose as well as the following electrolytes
NaCl: 2.338 g
Na acetate.3H$_2$O: 5.443 g
CaCl$_2$.2H$_2$O: 0.588 g
MgCl$_2$.6H$_2$O: 1.084 g
ZnCl$_2$ 0.009 g
KCl: 0.720 g
are added to this solution. After the pH value of the solution has been brought to 4.5–5.0 with L-malic acid, the mixture is made up to a volume of 1 liter with infusion water. The solution is sterilized at a temperature of 80° C.

This solution can also be formulated as a solution of 4% aminoacid content by dissolving 40% of the amounts of the various constituents in water and making up to 1 liter.

EXAMPLE 2

A nutrient solution of the composition shown below is prepared as described in Example 1, and is also sterilized at 80° C. The tyrosine is employed as acetyl-L-tyrosine.
L-Isoleucine: 3.500 g
L-Leucine: 6.000 g
L-Lysine: 6.500 g
L-Methionine: 1.900 g
L-Phenylalanine: 5.000 g
L-Threonine: 4.200 g
L-Tryptophane: 1.500 g
L-Valine: 6.000 g
L-Arginine: 8.000 g
L-Histidine: 6.000 g
L-Alanine: 16.000 g
L-Aspartic acid: 2.100 g
L-Cysteine: 0.390 g
L-Glutamic acid: 9.000 g
Glycine: 6.000 g
L-Ornithine: 2.500 g
L-Proline: 9.000 g
L-Serine: 4.500 g
L-Tyrosine: 1.500 g
L-Carnitine: 4.000 g
Fructose: 150.000 g
NaCl: 2.165 g
Na acetate.3H$_2$O: 5.850 g
Cacl$_2$.2H$_2$O: 0.506 g
MgCl$_2$.6H$_2$O: 0.932 g
ZnCl$_2$: 0.008 g
KCl: 0.770 g
Malic acid to adjust the pH value Infusion water to make up to 1,000 ml.

EXAMPLE 3

A solution of 4% aminoacid content is prepared analogously to Example 1 and is sterilized at 120° C. The solution has the following composition:
L-Isoleucine: 1.400 g
L-leucine: 2.400 g
L-Lysine: 2.600 g
L-Methionine: 0.760 g
L-Phenylalanine: 2.000 g
L-Threonine: 1.680 g
L-Tryptophane: 0.600 g
L-Valine: 2.400 g
L-Arginine: 3.200 g
L-Histidine: 2.400 g
L-Alanine: 6.400 g
L-Aspartic acid: 0.840 g
L-Cysteine: 0.390 g
L-Glutamic acid: 3.600 g
Glycine: 2.400 g
L-Ornithine: 1.000 g
L-Proline: 3.600 g
L-Serine: 1.800 g
L-Tyrosine: 0.600 g
L-Carnitine: 1.600 g
Sorbitol: 60.000 g
NaCl: 2.766 g
Na acetate.3H$_2$O: 4.680 g
CaCl$_2$.2H$_2$O: 0.353 g
MgCl$_2$.6H$_2$O: 0.651 g
ZnCl$_2$: 0.006 g
KCl: 0.537 g
L-Malic acid to adjust the pH
Infusion water to make up to 1,000 ml.

What we claim is:

1. An aqueous fat-free composition for the parenteral feeding and for the treatment of patients in the post-aggression phase in order to ensure an adequate supply of amino-acids consisting essentially of the following mixture:
    (a) glucose or glucose substitutes selected from the group consisting of fructose and sugar alcohols or a mixture of glucose and said glucose substitutes in at least an amount exceeding the normal body's demand and up to 50 parts by weight;
    (b) 0.8–1.2 parts by weight of L-carnitine as an inner salt or as a pharmaceutically tolerated acid addition salt; and
    (c) 25 parts by weight of an amino acid mixture composed of the following amino acids:
        0.8–1.05 parts by weight of L-isoleucine
        1.4–1.5 parts by weight of L-leucine
        1.4–1.65 parts by weight of L-lysine
        0.5–1.2 parts by weight of L-methionine
        1.25–1.4 parts by weight of L-phenylalanine
        0.7–1.05 parts by weight of L-threonine
        0.35–0.375 parts by weight of L-tryptophane
        1.0–1.5 parts by weight of L-valine
        2.0–2.8 parts by weight of L-arginine
        1.0–1.5 parts by weight of L-histidine
        3.5–4.0 parts by weight of L-alanine
        0.35–0.55 parts by weight of L-aspartic acid
        0.1 part by weight of L-cysteine
        2.0–2.25 parts by weight of L-glutamic acid
        1.5–2.3 parts by weight of glycine
        0–0.625 part by weight of ornithine
        2.2–2.8 parts by weight of L-proline
        1.1–1.4 parts by weight of L-serine
        0–1.5 parts by weight of L-tyrosine,
    the amino acids L-tyrosine and L-cysteine being present in the solution in the form of their acyl derivatives.

2. A composition according to claim 1 which additionally contains electrolytes selected from the group consisting of Na+, Ca++, Mg++, Zn++, K+, chloride-ions and acetate-ions in an amount sufficient to maintain the homeostasis and acid-base equilibrium in the body.

3. A composition according to claim 2, in which the amount of electrolyte is about 2.5 parts by weight per 25 parts by weight of aminoacids.

4. A composition according to claim 1, in which the concentration of the amino acid mixture is 3 to 10% per weight.

5. A process for complete parenteral feeding and treatment of a patient in the post aggression phase in order to ensure adequate supply with amino acids, comprising intravenously infusing said patient with the aqueous composition according to claim 1 in which an amount corresponding to 100 g of the amino acid mixture per day.

6. A process according to claim 5, in which the aqueous composition contains additionally electrolytes selected from the group consisting of $Na^+$, $Ca^{++}$, $Mg^{++}$, $Zn^{++}$, $K^+$, chloride ions and acetate ions in an amount sufficient to maintain the homeostasis and acid-base equilibrium in the body.

7. A process according to claim 6, in which the amount of the electrolytes present in the aqueous composition is about 2.5 parts by weight per B 25 parts by weight of the amino acids.

* * * * *